(12) United States Patent
Sata et al.

(10) Patent No.: US 8,962,832 B2
(45) Date of Patent: Feb. 24, 2015

(54) PROCESS FOR THE PREPARATION OF AMBRISENTAN AND NOVEL INTERMEDIATES THEREOF

(75) Inventors: Kaushik Babubhai Sata, Gujarat (IN); Bipin Pandey, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 316 days.

(21) Appl. No.: 13/382,988

(22) PCT Filed: Jul. 12, 2010

(86) PCT No.: PCT/IN2010/000464
§ 371 (c)(1),
(2), (4) Date: Mar. 19, 2012

(87) PCT Pub. No.: WO2011/004402
PCT Pub. Date: Jan. 13, 2011

(65) Prior Publication Data
US 2012/0184573 A1    Jul. 19, 2012

(30) Foreign Application Priority Data

Jul. 10, 2009  (IN) .......................... 1626/MUM/2009
Sep. 25, 2009  (IN) .......................... 2233/MUM/2009
Feb. 19, 2010  (IN) ............................ 462/MUM/2010

(51) Int. Cl.
*C07D 239/34*    (2006.01)

(52) U.S. Cl.
CPC .................................... *C07D 239/34* (2013.01)
USPC ........................................................ 544/318

(58) Field of Classification Search
USPC ........................................................ 544/318
See application file for complete search history.

(56) References Cited

U.S. PATENT DOCUMENTS

| | | |
|---|---|---|
| 5,703,017 A | 12/1997 | Baumann et al. |
| 5,932,730 A | 8/1999 | Reichers et al. |
| 6,559,338 B1 | 5/2003 | Bernard et al. |
| 7,109,205 B2 | 9/2006 | Riechers et al. |

FOREIGN PATENT DOCUMENTS

| | | |
|---|---|---|
| DE | 198 50 301 | 5/2000 |
| JP | H10-507190 | 7/1998 |
| JP | 2002-528524 | 9/2002 |
| WO | 2008/097468 | 8/2008 |
| WO | WO 2010/017918 | 2/2010 |
| WO | WO 2010/070658 | 6/2010 |
| WO | WO 2010/091877 | 8/2010 |

OTHER PUBLICATIONS

Anon.: "Crystalline and amorphous (2S)-2-(4, 6-dimethyl-s-pyrimidinyl )oxy-3-methoxy- 3,3-diphenylpropanoic acid and process for preparation thereof", IP. Com Journal, 9(5A), 10, (Apr. 21, 2009).

Anon.:, "Optical resolution of 2-hydroxy-3-methoxy-3, 3-diphenylpropionic acid an intermediate of (2S)-2-(4, 6-dimethylpyriidin-2-yl)oxy-3-methoxy-3,3- diphenylpropanoic acid", IP. Com Journal, 9(12B), 30, (Dec. 15, 2009).

International Search Report for PCT/IN2010/000464, mailed Jan. 13, 2011.

International Preliminary Report on Patentability for PCT/IN2010/000464, dated Jan. 11, 2011.

Anon.:, "Optical resolution of 2-hydroxy-3-methoxy-3, 3-diphenylpropionic acid an intermediate of (2S)-2-(4,6-dimethylpyriidin-2-yl)oxy-3-methoxy-3,3- diphenylpropanoic acid", IP. Com Journal, 9(12B), 30, (Dec. 15, 2009).

Jansen, R., et al., "Structural Similarity and Its Surprises: Endothelin Receptor Antagonists-Process Research and Development Report," *Organic Process Research & Development*, 5:16-22 (2001).

Office Action issued in corresponding Japanese Patent Application No. 2012-519124 (now JP Patent No. 5531097, dated Nov. 26, 2013 with English Translation (7 pages).

*Primary Examiner* — Deepak Rao
(74) *Attorney, Agent, or Firm* — Nixon & Vanderhye P.C.

(57) ABSTRACT

The invention relates to improved processes for the preparation of ambrisentan. The invention also relates to a novel intermediate useful in the preparation of ambrisentan and a process for the preparation of the intermediate. The invention also relates to new polymorphic form of ambrisentan. In particular, it relates to a polymorphic form, designated as Form I of ambrisentan and a process for the preparation of the Form I.

7 Claims, 4 Drawing Sheets

PROCESS FOR THE PREPARATION OF AMBRISENTAN AND NOVEL INTERMEDIATES THEREOF

This application is the U.S. national phase of International Application No. PCT/IN2010/000464, filed 12 Jul. 2010, which designated the U.S. and claims priority to India Application No. 1626/MUM/2009, filed 10 Jul. 2009; India Application No. 2233/MUM/2009, filed 25 Sep. 2009; and India Application No. 462/MUM/2010, filed 19 Feb. 2010, the entire contents of each of which are hereby incorporated by reference.

FIELD OF INVENTION

The present invention provides an improved process for the preparation of Ambrisentan. The present invention also provides a novel intermediate for the preparation of Ambrisentan and a process for the preparation of the intermediate. The invention also describes a new crystalline form of Ambrisentan.

BACKGROUND OF THE INVENTION

Ambrisentan, a potent selective endothelin receptor antagonist, is utilized for the treatment of pulmonary arterial hypertension and idiopathic pulmonary fibrosis. It blocks the endothelin receptor on vascular smooth muscle cells and cardiac myocytes, preventing vasoconstriction and smooth muscle proliferation.

Ambrisentan is marketed under the trade name Letairis™ or Volibris®. Ambrisentan is chemically known as (S)-2-((4,6-dimethylpyrimidin-2-yl)oxy)-3-methoxy-3,3-diphenyl propanoic acid and has the structural formula as shown in formula (I).

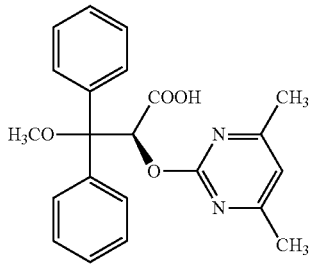

U.S. Pat. No. 5,703,017 broadly discloses several molecules generally, which are 3-(Het) aryl carboxylic acid derivatives. The compounds disclosed also include Ambrisentan. In the specification, synthetic schemes for preparation of the molecules and for their intermediates are disclosed. The general methods of preparation involve coupling the epoxide of formula III (for example, with R=COOR) with alcohols or thiols of formula IV according to the following scheme:

Scheme 1

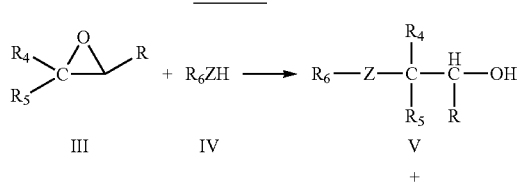

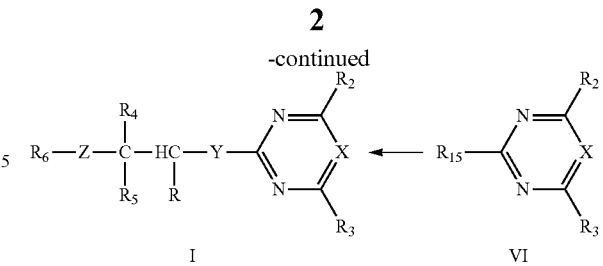

U.S. Pat. No. 7,109,205 discloses and claims Ambrisentan. The patent also discloses the process for the preparation of Ambrisentan as per a similar scheme as in the above patent. This specification also discloses the preparation of Ambrisentan according to the above process.

This patent also describes the preparation in laboratory scale of (S)-2-hydroxy-3-methoxy-3,3-diphenylpropanoic acid (compound V) by resolution of the corresponding racemate using L-proline methyl ester and (S)-1-(4-nitrophenyl) ethylamine. By this resolution, yield of 35% based on the racemate and an optical purity of 99.8% were achieved.

U.S. Pat. No. 6,559,338 describe a process of resolution of 2-hydroxypropanoic acid by using an optically active base (S)-1-(4-chlorophenyl)ethylamine and then one of the diastereomeric salts formed is separated off. However the optically active base used here is very expensive and would not be preferable for large-scale production. Additionally, the objective of this resolution has not been clearly defined.

However, the U.S. Pat. No. 6,559,338 also state that, it has been found that when this described reaction step was scaled up (several kg to 100 kg), additional working steps became necessary in order to ensure a high optical purity. The diastereomeric salt of (S)-2-hydroxypropanoic acid and (S)-1-(4-nitrophenyl)ethylamine crystallizes with difficulty and therefore cannot be filtered off readily either, so that some of the mother liquor remains in the crystals together with the enantiomer to be separated off. Only when the crystals were additionally stirred in the tank together with fresh solvent, and when the crystals that had been filtered off are copiously rewashed, the required optical purity was obtained.

Therefore, the present invention provides a process for resolution of racemic 2-hydroxy-3-methoxy-3,3-diphenyl-propanoic acid (VIII) that does not have the above-mentioned disadvantages but can readily be carried out on an industrial scale.

In addition, the inventors of the present invention surprisingly found the improved resolution of the racemate compound (VIII) by reacting the racemic acid with a suitable optically active amine and subsequently separating off the diastereomeric salt with high chiral purity. Additionally the same diastereomeric salt can further be utilized for the preparation of Ambrisentan.

Thus, the present invention discloses an improved process for preparing Ambrisentan. The present invention discloses an improved process for preparing Ambrisentan wherein the chiral amine base used as resolving agent, provides a novel intermediate that is used in preparation of Ambrisentan of high enantiomeric purity.

WO2010017918 disclosed the amorphous form of Ambrisentan and process for the preparation of thereof. It is well known that amorphous forms have several limitations in terms of stability, processability etc. thereby making the crystalline form of any compound more preferable. The present inventors have surprisingly found a new crystalline form of Ambrisentan which is stable, easily processable & can be used to obtain the commercial form of Ambrisentan in chirally and chemically pure form.

SUMMARY OF THE INVENTION

Figure 1:
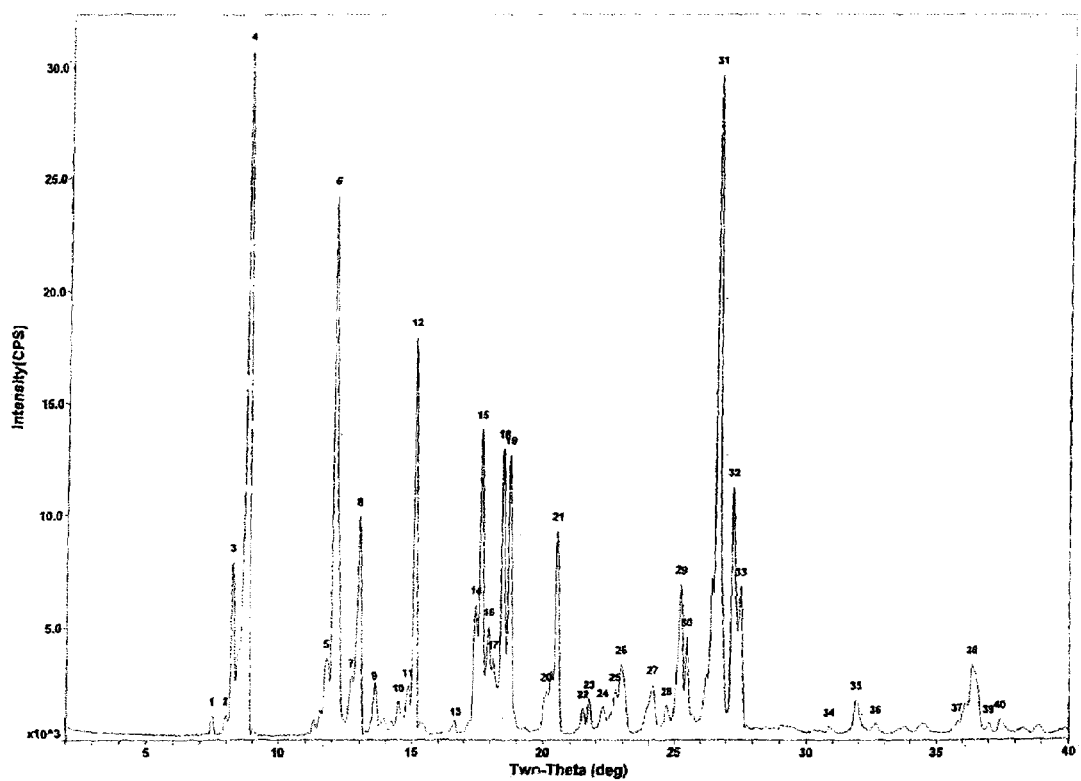
FIG. 1 is a powder X-ray diffraction (XRPD) pattern of the crystalline Ambrisentan according to the present invention.

In one general aspect there is provided a novel process for the preparation of Ambrisentan. The process includes:

a) resolving 2-hydroxypropanoic acids of formula (VIII),

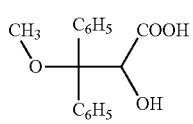

Formula VIII with optically active chiral amine base of formula (IX),

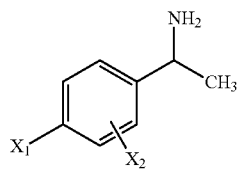

Formula IX where the resolving agent amine is with either in (S) or (R) configuration, $X_1$ is selected from hydrogen, halogen, nitro, $(C_1-C_4)$ alkyl or $(C_1-C_4)$ alkoxy group, and $X_2$ at each occurrence is independently selected from hydrogen, halogen, nitro a $(C_1-C_4)$ alkyl or $(C_1-C_4)$ alkoxy group, in suitable solvent to obtain a diastereomeric salt of 2-hydroxypropanoic acids of formula (II)

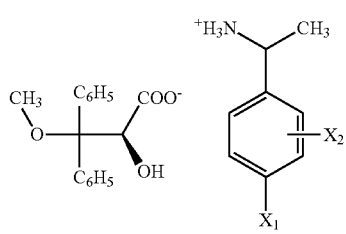

Formula II b) reacting diastereomeric salt of 2-hydroxypropanoic acids of formula (II) with 4,6-dimethyl-2-(methylsulfonyl)pyrimidine (VII),

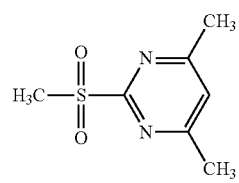

Formula VII to obtain ambrisentan.

Embodiments of the process may include one or more of the following features. For example, the resolution of racemic 2-hydroxypropanoic acid of Formula (VIII) may be carried out in the presence of one or more suitable solvents. The reaction of the diastereomeric salt of 2-hydroxypropanoic acid of Formula (II) with 4,6-dimethyl-2-(methylsulfonyl) pyrimidine of Formula (VII) may be carried out in the presence of one or more suitable bases in one or more suitable solvents. The diastereomeric salt of 2-hydroxypropanoic acid of Formula (II) may be recrystallized from solvents prior to condensation with 4,6-dimethyl-2-(methylsulfonyl)pyrimidine of Formula (VII).

In another general aspect, there is provided a compound of formula (II),

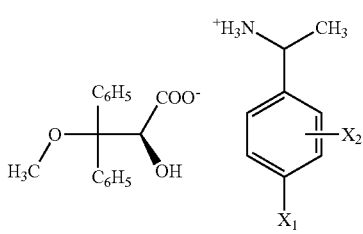

II where the resolving agent amine is with either in (S) or (R) configuration, $X_1$ is selected from hydrogen, halogen, nitro, $(C_1-C_4)$ alkyl or $(C_1-C_4)$ alkoxy group, and $X_2$ at each occurrence is independently selected from hydrogen, halogen, nitro a $(C_1-C_4)$ alkyl or $(C_1-C_4)$ alkoxy group.

In another aspect there is provided a process for the purification of ambrisentan. The process includes obtaining a solution of ambrisentan in one or more suitable solvents and recovering the pure ambrisentan by removal of the solvents.

Removing the solvent may include, for example, one or more of distillation, distillation under vacuum, evaporation, filtration, filtration under vacuum, decantation and centrifugation.

Embodiments of the process may include one or more of the following features. For example, the solution of ambrisentan may be obtained by heating or stirring, or a combination of both. Alternatively, the solution may be obtained by adding a suitable base and acidifying the solution so obtained with a suitable acid until pH about 2-3.

The product so obtained may be further or additionally purified to obtain desired purity levels.

The process may include further forming the product so obtained into a finished dosage form.

The process may produce the pure ambrisentan having a purity of more than 99% and a chiral purity of more than 99.8% by HPLC.

In another general aspect there is provided a novel polymorphic form of ambrisentan, hereinafter designated as Form I.

Figure 2:
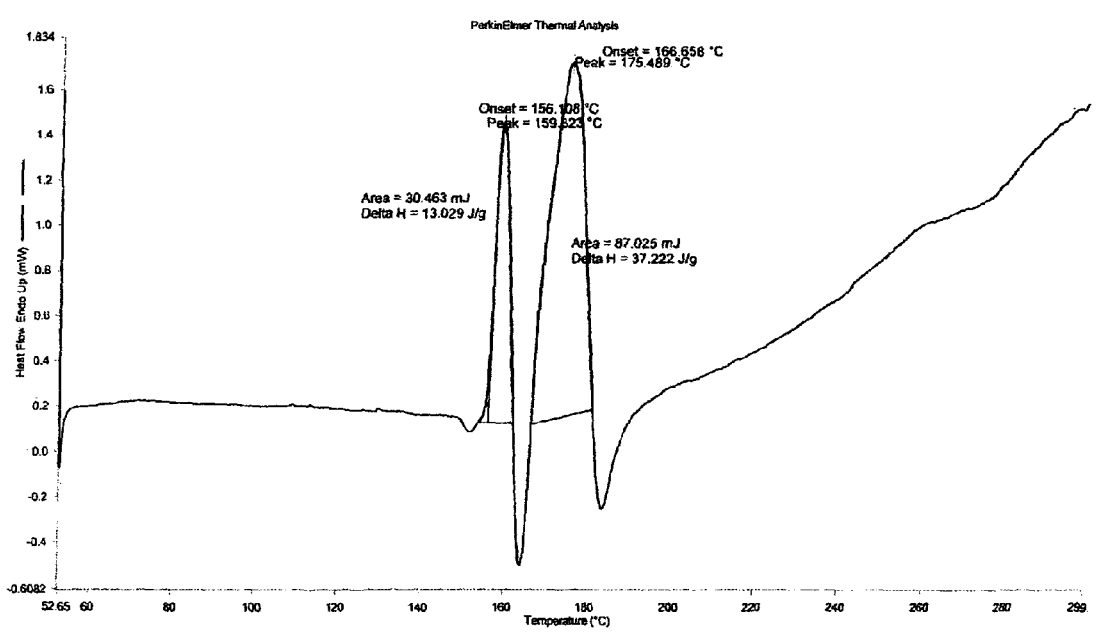
FIG. 2 is a Differential scanning calorimetry of crystalline Ambrisentan according to the present invention.

The polymorphic form of ambrisentan may have the X-ray diffraction pattern of FIG. 1 and Differential Scanning calorimetry graph of FIG. 2.

In another general aspect there is provided a process for preparing the polymorphic Form I of ambrisentan. The process includes obtaining a solution of ambrisentan in one or more suitable solvent(s); optionally, adding a suitable anti-solvent(s) to the solution; and isolating the Form I of ambrisentan by removing the solvents.

Removing the solvents may include, for example, one or more of filtration, filtration under vacuum, evaporation, decantation, and centrifugation and other suitable techniques as known to a person skilled in the art.

Embodiments of the process may include one or more of the following features. For example, the solution may be concentrated before adding the anti-solvent. The solution may be cooled before removing the solvents.

The product obtained may be further or additionally dried to achieve the desired moisture values. For example, the product may be further or additionally dried in a tray drier, dried under vacuum and/or in a Fluid Bed Drier.

In another aspect there is provided a pharmaceutical composition comprising a therapeutically effective amount of polymorphic Form I of ambrisentan, and one or more pharmaceutically acceptable carriers, excipients or diluents.

In another general aspect there is provided a novel polymorphic form of (S)-3-methoxyphenylethylammonium (S)-2-hydroxy-3-methoxy 3,3-diphenyl propionate of formula (IIa). The polymorphic form of formula (IIa) may have the X-ray diffraction pattern of FIG. 3

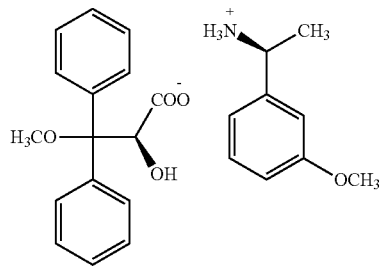

Formula (IIa)

In another general aspect there is provided a novel polymorphic form of (R)-2,4-dichlorophenylethylammonium (S)-2-hydroxy-3-methoxy 3,3-diphenyl propionate of formula (IIb). The polymorphic form of formula (IIb) may have the X-ray diffraction pattern of FIG. 4.

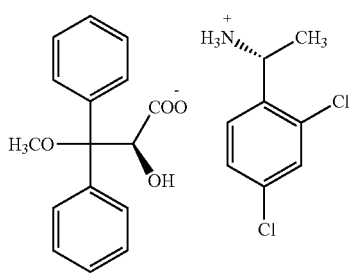

Formula (IIb)

The details of all the embodiments of the inventions are set forth in the description below. Other features, objects and advantages of the inventions will be apparent from the description.

DETAILED DESCRIPTION

As used herein, the term "THF" refers to tetrahydrofuran, the term "DCM" refers to dichloromethane, the term "DMF" refers to dimethyl formamide, the term "DIPE" refers to diisopropyl ether, the term "DMSO" refers to dimethyl sulfoxide, the term "LHMDS" refers to Lithium hexamethyl disilazide, the term "KHMDS" refers to Potassium hexamethyl disilazide and the term "MTBE" refers to Methyl tertiary butyl ether, the term "(S)-3-Methoxy PEA" refers to (S)-1(3-methoxyphenyl)ethylamine and the term "(R)/(S)-2,4-dichloro PEA" refers to (R)/(S)-1(2,4-dichlorophenyl) ethylamine, the term "(S)-4 chloro PEA" refers to (S)-1-(4-chlorophenyl)ethylamine Purity of diastereomeric salt (R)/(S)-2,4-dichlorophenylethylammonium (S)-2-hydroxy-3-methoxy-3,3-diphenyl propionate or (S)-3-mthoxypehenylethyl ammonium (S)-2-hydroxy-3-methoxy-3,3-diphenyl propionate refers to the purity of related propionic acid.

The inventors have developed a process for the preparation of Ambrisentan using novel intermediate of formula (II) by resolving 2-hydroxypropanoic acid of Formula (VIII), a) resolving 2-hydroxypropanoic acids of formula (VIII),

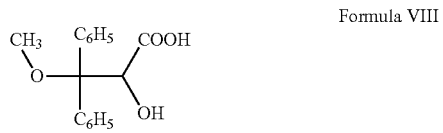

Formula VIII with optically active chiral amine base of formula (IX),

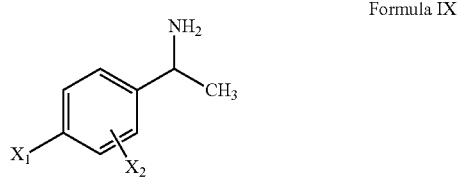

Formula IX where the resolving agent amine is with either in (S) or (R) configuration, $X_1$ & $X_2$ are as defined earlier, in suitable solvent to give diastereomeric salt of 2-hydroxypropanoic acids of formula (II), and

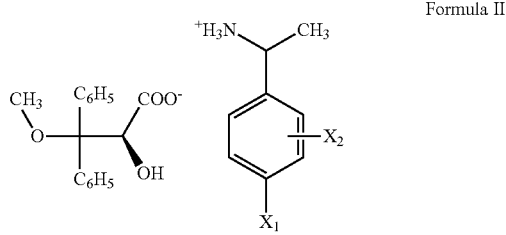

Formula II b) reacting the diastereomeric salt of 2-hydroxypropanoic acids of Formula (II) with either in (S) or (R) configuration, $X_1$ & $X_2$ are as defined earlier, with 4,6-dimethyl-2-(methylsulfonyl)pyrimidine (VII) in presence of a suitable base, to obtain the ambrisentan.

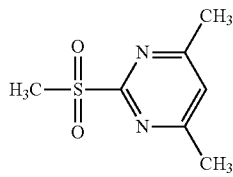

Formula VII

In general, the reaction of 2-hydroxypropanoic acids (VIII) with optically active chiral amine base of formula (IX), with either in (S) or (R) configuration, $X_1$ & $X_2$ are as defined earlier may be carried out in the presence of one or more suitable solvent. Suitable solvents which can be used for above resolution may include one or more of water, DMSO, DMF, acetonitrile, diethyl ether, 1,4-dioxane, MTBE, 2-methyl THF, dimethyl acetamide, DCM, DIPE, THF, ($C_1$-$C_6$) alcohols such as ethanol, methanol, isopropanol, tert-butanol and the like. Mixtures of all of these solvents are also contemplated.

The reaction of diastereomeric salt of 2-hydroxypropanoic acids (II) with 4,6-dimethyl-2-(methylsulfonyl)pyrimidine (VII) may be carried out in presence of suitable base in one or more suitable solvent.

Suitable bases which can be used for above coupling may include one or more of lithium diisopropyl amide, sodium amide, sodium carbonate, sodium bicarbonate, potassium carbonate, sodium hydroxide, potassium hydroxide, tripotassium phosphate, LHMDS, KHMDS, potassium tert butoxide, sodium tert butoxide and the like.

Suitable solvents which can be used may include one or more of DMSO, DMF, acetonitrile, acetone, diethyl ether, 1,4-dioxane, 2-methyl THF, dimethyl acetamide, DCM, DIPE, THF and the like or mixture thereof.

In another aspect, a novel intermediate of Formula (II) used in the preparation of ambrisentan is provided,

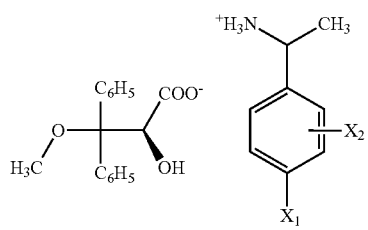

II with either in (S) or (R) configuration, $X_1$ is selected from hydrogen, halogen, nitro, ($C_1$-$C_4$) alkyl or ($C_1$-$C_4$) alkoxy group, and $X_2$ at each occurrence is independently selected from hydrogen, halogen, nitro a ($C_1$-$C_4$) alkyl or ($C_1$-$C_4$) alkoxy group.

In another aspect, a process for the preparation of the novel intermediate of Formula (II), as a diastereomeric salt is provided, by resolving racemic 2-hydroxypropanoic acid of Formula (VIII) with an optically active chiral amine of Formula (IX), with either in (S) or (R) configuration, $X_1$ & $X_2$ are as defined earlier, in suitable solvent.

In general, the reaction of 2-hydroxypropanoic acids (VIII) with optically active chiral amine base of formula (IX) with either in (S) or (R) configuration, $X_1$ & $X_2$ are defined earlier may be carried out in the presence of suitable solvent.

Suitable solvents which can be used for above resolution may include one or more of water, DMSO, DMF, acetonitrile, diethyl ether, 1,4-dioxane, MTBE, 2-methyl THF, dimethyl acetamide, DCM, DIPE, THF, ($C_1$-$C_6$) alcohols such as ethanol, methanol, isopropanol, tert-butanol and the like or suitable mixtures thereof.

Alternatively, the other enantiomer i.e. R-isomer of 2-hydroxypropanoic acid can also be prepared by resolution with suitable optically active base.

The inventors also have developed a process for the purification of ambrisentan by obtaining a solution of ambrisentan in one or more suitable solvents and recovering the pure ambrisentan by removal of the solvents.

The ambrisentan may be prepared according to the present invention or may be prepared by any of the methods known in the art.

The term "solvent" includes one or more of alcohols, esters, chlorinated solvents, nitriles, ketones, ethers, aprotic polar solvents or mixtures thereof.

The solution of ambrisentan in a solvent can be obtained by dissolving, slurrying, stirring, or a combination thereof. The solution of ambrisentan may be obtained by heating the solvent. It may be heated from about 25° C. to reflux temperature. The solution of ambrisentan can also be obtained by suspending ambrisentan in water and adding a solution of one or more suitable bases.

The resultant solution can be clarified to remove foreign particulate matter or treated with activated charcoal to remove coloring and other related impurities.

The solution may be cooled before removing the solvents. The solution may be acidified with suitable aqueous solution of acids to precipitate ambrisentan.

Suitable bases which can be used may include one or more of carbonates, bicarbonates or alkali bases. The acids used may be organic acids, for example, acetic acid, formic acid, and the like, or inorganic acids, for example, dilute hydrochloric acid or dilute sulfuric acid.

The solvent may be removed by a technique which includes, for example, distillation, distillation under vacuum, evaporation, filtration, filtration under vacuum, decantation and centrifugation.

The product obtained may be further or additionally dried to achieve the desired moisture values. For example, the product may be further or additionally dried in a tray drier, dried under vacuum and/or in a Fluid Bed Drier.

The pure ambrisentan has a purity of more than 99% and a chiral purity more than 99.8% by HPLC.

The inventors also have developed a process for the preparation of a novel polymorphic form of ambrisentan, designated as Form I, by obtaining a solution of ambrisentan in one or more solvents; optionally, adding one or more suitable anti-solvents; and isolating the Form I of ambrisentan by removing the solvents.

The term "obtaining" includes mixing, adding, slurrying, stirring, heating, or a combination thereof. The solution of ambrisentan may be obtained by heating the solvent. It may be heated from about 25° C. to reflux temperature. The resultant solution can be clarified to remove foreign particulate matter or treated with activated charcoal to remove coloring and other related impurities. The solution so obtained may be concentrated to reduce the amount of solvent. The solution may be concentrated by removing the solvent completely to get a residue. The solvent may be removed under reduced pressure, to obtain crystalline ambrisentan.

A suitable anti-solvent may be added to the solution to precipitate the ambrisentan. The solution may be heated after adding the anti-solvent.

In one aspect, the solution may be cooled before removing the solvents.

The ambrisentan to be used as the starting material for preparation of the novel polymorph can be prepared by any process known in the literature or may be obtained by the process of the present invention.

The solution of ambrisentan may be prepared in one or more solvents, including, for example, alcohols, esters, chlorinated solvents, nitriles, ketones, ethers, aprotic polar solvents, and suitable mixtures of one or more of these solvents.

In general, any solvent can be used as an anti-solvent in which ambrisentan is insoluble, practically insoluble or very slightly soluble. The terms insoluble, practically insoluble and very slightly soluble have their ordinary meanings as defined in United States Pharmacopoeia 2002. For example, suitable anti-solvents which may be used include non polar solvent such as hydrocarbons and water or a mixture thereof.

The novel polymorphic Form I of ambrisentan may exhibit characteristic 2-theta values at about 7.462, 8.239, 11.781, 12.703, 13.587, 14.842, 16.703, 17.660, 18.120, 18.740, 20.518, 21.741, 22.722, 24.139, 25.221, 26.641, 27.521, 30.860±0.2 degrees 2θ. The PXRD pattern of Form I of ambrisentan may further exhibit characteristic 2-theta values at about 7.980, 8.781, 12.08, 12.999, 14.499, 15.100, 17.441, 17.939, 18.499, 20.120, 21.499, 22.261, 22.959, 24.701, 25.461, 27.241, 37.440±0.2 degrees 2θ.

Further, Form I of ambrisentan may exhibit a Differential Scanning Calorimetry graph having endothermic peaks at about 156.1° C.±2° C. and about 166.6° C.±2° C.

The polymorphic Form I of ambrisentan may be formulated into ordinary dosage forms such as, for example, tablets, capsules, pills, solutions, etc. In these cases, the medicaments can be prepared by conventional methods with conventional pharmaceutical excipients.

Alternatively, the intermediate of Formula (II) may be purified by obtaining a solution of the novel intermediate of Formula (II) in one or more suitable solvents, adding a suitable anti-solvent to the solution; and isolating the pure novel intermediate of Formula (II).

In general, any solvent can be used as an anti-solvent in which the novel intermediate of Formula (II) is insoluble, practically insoluble or very slightly soluble. The terms insoluble, practically insoluble and very slightly soluble have their ordinary meanings as defined in United States Pharmacopoeia 2002. For example, suitable anti-solvents which may be used include hexane, pentane, hexane, heptane, petroleum ether, methyl t-butyl ether, cyclohexane, toluene, diethyl ether and octane, water or mixture thereof.

In one of the preferred embodiments the preferable compound from the compound of formula (II) are (S)-3-methoxyphenylethylammonium (S)-2-hydroxy-3-methoxy 3,3-diphenyl propionate of formula (IIa) and (R)-2,4-dichlorophenylethylammonium (S)-2-hydroxy-3-methoxy 3, 3 diphenyl propionate of formula (IIb).

In an embodiment, the invention is provided a novel polymorphic form of (S)-3-methoxyphenylethylammonium (S)-2-hydroxy-3-methoxy 3,3-diphenyl propionate of formula (IIa). The polymorphic form of formula (IIa) may have the X-ray diffraction pattern of FIG. 3

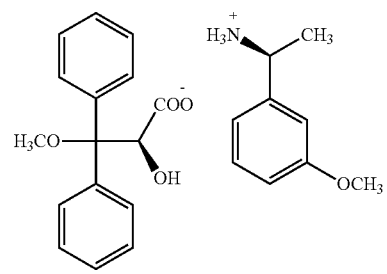

Formula (IIa)

The novel polymorphic form of the (S)-3-methoxyphenylethylammonium (S)-2-hydroxy-3-methoxy 3,3-diphenyl propionate of formula (IIa) exhibits characteristic 2.theta. values at about 7.05, 10.15, 12.15, 13.87, 17.86, 23.01 and 24.80±0.2 degrees 2θ. The PXRD pattern of (S)-3-methoxyphenylethylammonium (S)-2-hydroxy-3-methoxy 3,3-diphenyl propionate of formula (IIa) further exhibits characteristic 2.theta. values at about 8.39, 11.39, 13.87, 18.87, 21.90 and 24.18±0.2 degrees 2θ.

In an another embodiment, the invention is provided a novel polymorphic form of (R)-2,4-dichlorophenylethylammonium (S)-2-hydroxy-3-methoxy 3,3-diphenyl propionate of formula (IIb). The polymorphic form of formula (IIb) may have the X-ray diffraction pattern of FIG. 4.

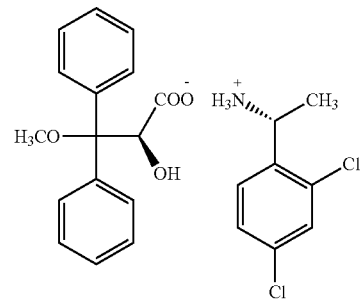

Formula (IIb)

The novel polymorphic form of the (R)-2,4-dichlorophenylethylammonium (S)-2-hydroxy-3-methoxy 3,3 diphenyl propionate of formula (IIb) exhibits characteristic 2.theta. values at about 8.49, 11.51, 11.88, 17.00, 18.74, 21.13 and 23.03±0.2 degrees 2θ. The PXRD pattern of (R)-2,4-dichlorophenylethylammonium (S)-2-hydroxy-3-methoxy 3,3 diphenyl propionate of formula (IIb) further exhibits characteristic 2.theta. values at 10.22, 12.22, 13.89, 14.30, 19.25, 20.49, 24.14, 25.48 and 34.13±0.2 degrees 2θ.

Analytical Processes:

The complete x-ray powder spectrum was recorded with a Rigaku D/Max 2200 VPC X-ray powder diffractometer model using copper radiation. The X-ray diffraction pattern was recorded by keeping the instrument parameters as below:

X-ray: Cu/40 kv/30 mA, Diverging slit: 1°, Scattering slit: 1°, Receiving slit: 0.15 mm, Monochromator RS: 0.8 mm, Counter: Scintillation counter, Scan mode: Continuous, Scan speed: 3.000°/min., Sampling width: 0.020°, Scan axes: 2 theta vs. CPS, Scan range: 2° to 40.0°, Theta offset: 0.000

Differential scanning calorimetric analysis was carried out in a DSC-60 model from Shimadzu (S/W: TA-60WS Aquisition version 2.1.0.0) by keeping following parameters, Sample Size Approx. 1-2 mg, Sample Pans: Hermetic/Crimping Pans, Start Temperature: 50° C., End Temperature: 300° C., Rate of Heating: 10° C./min., Purge Gas: Nitrogen, Flow rate: 20 ml/min The invention is further illustrated by the following examples, which are provided merely to be exemplary of the invention and do not limit the scope of the invention. Certain modifications and equivalents will be apparent to those skilled in the art and are intended to be included within the scope of the invention.

EXAMPLE 1

Preparation of
(R)-2,4-dichlorophenylethylammonium
(S)-2-hydroxy-3-methoxy 3,3 diphenyl propionate

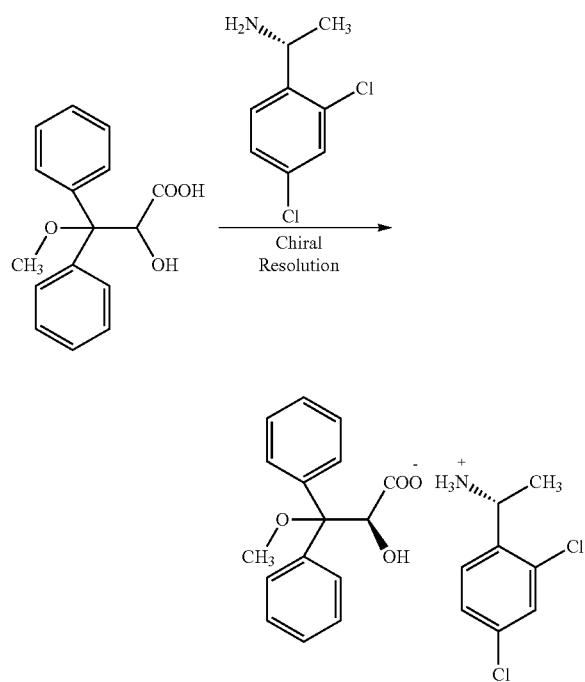

In a 25 mL three neck flask, attached with stirrer, thermometer; condenser with guard tube, over water bath, (1 g) racemic 2-hydroxy-3-methoxy 3,3 diphenyl propanoic acid and 10 mL methyl t-butyl ether was added at room temperature and stirred for 5 min. To the clear yellow solution, 10 mL methanol was added and then heated. Solution was refluxed gently. To this reaction mixture of (0.349 gm) (R)-2,4-dichloro PEA and 6 mL methyl t-butyl ether was added. The solution was refluxed for 1 hour to obtain clear solution and clear solution was allowed to cool naturally. The solution was stirred at room temperature for 3 hrs. Solid material was filtered, washed with 5 mL methyl t-butyl ether and dried.

Yield 212 mg. (24.96%), HPLC purity: 99.9%, Chiral purity: 99.4%.

EXAMPLE 2

Preparation of
(S)-2,4-dichlorophenylethylammonium
(R)-2-hydroxy-3-methoxy 3,3 diphenyl propionate

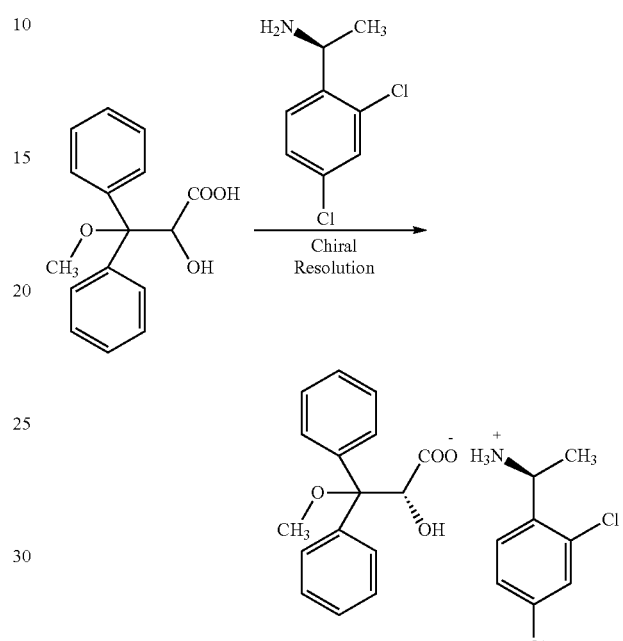

In a 50 mL three neck flask, attached with stirrer, thermometer, condenser with guard tube, over water bath (1 g) racemic 2-hydroxy-3-methoxy 3,3 diphenyl propanoic acid and 10 mL methyl t-butyl ether at room temperature was added and stirred for 5 min. To the clear yellow solution, 10 mL methanol was added and then heated. Solution was refluxed gently.

To this reaction, mixture of (0.454 g) (S)-2,4-dichloro PEA and 6 mL methyl t-butyl ether was added. The solution was refluxed for 1 hour and hazy solution was allowed to cool naturally. The hazy solution was stirred at room temperature for 3 hrs. Solid material was filtered, washed with 5 mL methyl t-butyl ether and dried. Yield: 298 mg. (35%). HPLC purity: 99.9%. Chiral purity: 99.3%.

Similarly, (S)-2,4-dichlorophenylethylammonium (R)-2-hydroxy-3-methoxy 3,3 diphenyl propionate was prepared in different batches and the results are summarized in table 1 given below.

TABLE 1

| Ex No. | Chiral amine | Input* g | Output g | % Purity HPLC | % Purity Chiral | % Yield | Solvent |
|---|---|---|---|---|---|---|---|
| 3 | (S))-2,4-Dichloro PEA | 4.4 | 1.5 | 99.95 | 98.38 | 40.15 | Solvent MTBE + MeOH |

*Input refers to propionic acid deriv.

EXAMPLE 4

Preparation of Ambrisentan

In a 25 mL three neck flask with stirring arrangement, (1 gm) (R)-2,4-dichlorophenylethyl ammonium (S)-2-hydroxy-3-methoxy-3,3-diphenylpropionate and (0.622 gm) sodium tertiary butoxide (6.488 mmol) in 10 ml DMF at 25° C. were taken and stirred for 5 min. (0.604 gm) 4,6-dimethyl-2-(methylsulfonyl)pyrimidine (3.244 mmol) was added to the reaction mixture in one lot. The reaction mixture was stirred at room temperature for 4 hours and subsequently dumped into cold water and aqueous layer was washed with toluene. Aqueous layer was collected and acidified with HCl to adjust pH to 2. Solid white material was precipitated. Solid white material was precipitated. The solid so obtained was filtered, washed with water and dried.

Yield: 0.62 gm (75.7%), HPLC Purity: 98.73%, Chiral Purity: 100%

EXAMPLE 5

Preparation of Ambrisentan

In a 25 mL three neck flask with stirring arrangement, (1 gm) (R)-2,4-dichlorophenylethyl ammonium (S)-2-hydroxy-3-methoxy-3,3-diphenylpropionate and (0.726 gm) potassium tertiary butoxide (6.488 mmol) in 10 ml DMF at 25° C. were taken and stirred for 5 min. (0.604 gm) 4,6-dimethyl-2-(methylsulfonyl)pyrimidine (3.244 mmol) was added to the reaction mixture in one lot. The reaction mixture was stirred at room temperature for 6 hours and subsequently dumped into cold water and washed the aqueous layer with toluene. Aqueous layer was collected and acidified with HCl to pH 2. The solid was extracted with ethyl acetate, and wash the ethyl acetate layer with water followed by brine. Dry over sodium sulphate and concentrated on Buchi Rotavapor.

Yield: 0.4 gm, HPLC Purity: 63.05%

EXAMPLE 6

Preparation of (S)-3-methoxyphenylethyl ammonium (S)-2-hydroxy-3-methoxy-3,3-diphenyl propionate

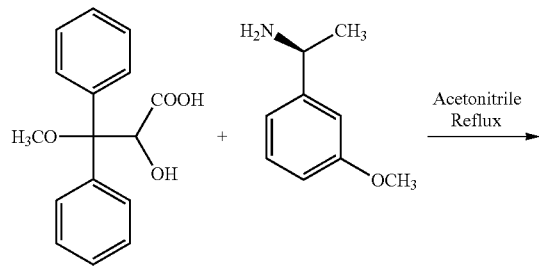

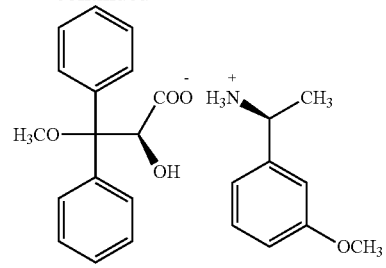

In a 50 mL three necked flask, equipped with a magnetic stirrer, water condenser, thermometer and addition funnel, (0.5 g) (1.84 m.mole) 2-hydroxy-3-methoxy-3,3-diphenyl propanoic acid and 5 ml acetonitrile at 25-30° C. was charged. The clear reaction mixture was heated at reflux. Subsequently, (0.166 g) (1.10 mmol) (S)-3-methoxy PEA diluted in acetonitrile was added drop wise to the reaction mixture at reflux temperature. Solid was precipitated within 5-10 minutes and then after the precipitated solid was stirred at reflux temperature for 0.5 hours. Further the reaction mixture was cooled gradually at 25-30° C. and stirred for 1.5 hrs. The solid was filtered and washed with acetonitrile, and dried.

Yield: 0.295 g (75.9%), HPLC Purity: 99.46%, Chiral Purity: 98.39

EXAMPLE 7

Preparation of Ambrisentan

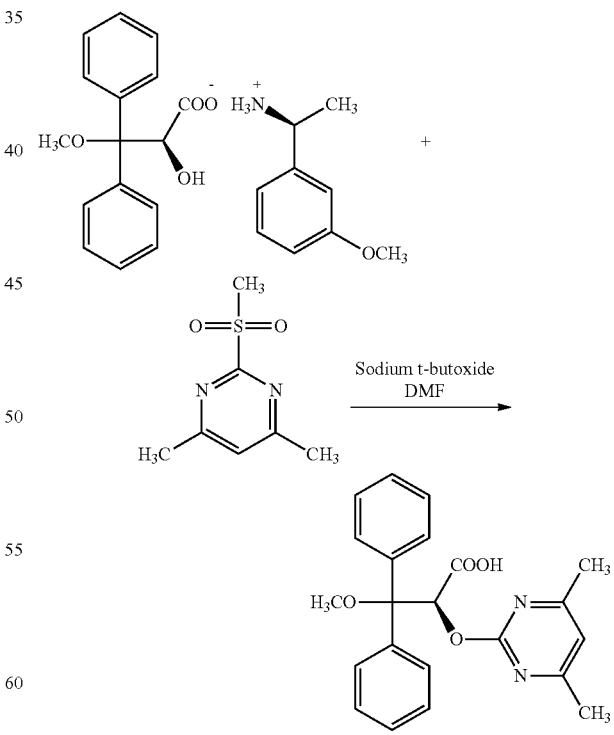

In a 25 mL three necked flask with stirring arrangement, (0.2 gm) (S)-3-methoxyphenylethyl ammonium (S)-2-hydroxy-3-methoxy-3,3-diphenylpropionate (0.47 mmol) and (0.136 gm) sodium tertiary butoxide (1.417 mmol) in 2 mL DMF (10 volumes) at 25° C. was taken and stirred for 5 min. Subsequently, 0.132 gm 4,6-dimethyl-2-(methylsulfonyl)pyrimidine (0.708 mmol) was added to the reaction mixture in one lot. The reaction mixture was stirred at room temperature for 1.5 hours and subsequently dumped into cold water and which on suitable work-up give the solid Ambrisentan.

Yield: 0.09 gm (50.33%), HPLC Purity: 97.98%, Chiral Purity: 98.33%

EXAMPLE 8

Process for the Preparation of Crystalline Form of Ambrisentan

In a 500 mL three necked flask with stirring and refluxing arrangement, (17.5 gm) crude Ambrisentan was taken in 122.5 ml absolute ethanol and refluxed to obtain clear solution. Subsequently, 87.5 ml DM water was added and further refluxed for 20 minutes to obtain clear solution. The reaction mixture was kept at room temperature for 24 hours. Crystalline solid was obtained. The solid was filtered, washed with 50% ethanol and dried.

Yield: 14.7 g (84%), HPLC purity: 99.84%, chiral purity: 100.0%

The crystalline form of Ambrisentan was characterized by PXRD peaks at about 7.462, 7.980, 8.239, 8.781, 11.781, 12.080, 12.703, 12.999, 13.587, 14.499, 14.842, 15.100, 16.703, 17.441, 17.660, 17.939, 18.120, 18.499, 18.740, 20.120, 20.518, 21.499, 21.741, 22.261, 22.722, 22.959, 24.139, 24.701, 25.221, 25.461, 26.641, 27.241, 27.521, 30.860, 31.901, 32.659, 35.803, 36.360, 37.003, 37.440±0.2-theta (FIG. 1) Similarly the crystalline form of Ambrisentan is prepared by using solvent such as ethanol, THF, MIBK and isopropyl alcohol following similar procedure as above.

EXAMPLE 9

Preparation of Amorphous Ambrisentan

In 25 mL three necked flask, (0.2 gm) Ambrisentan and 1 ml 10% sodium hydroxide solution was taken. The reaction mixture was stirred to get clear solution, charcoalised and then acidified with HCl to pH 2. Solid white material was precipitated. The solid mass was filtered and washed with water till neutral. It was dried.

Yield: 0.14 gm (70%), HPLC Purity: 99.82%, Chiral Purity: 98.34%

EXAMPLE 10

Preparation of (S)-3-methoxyphenylethylammonium (S)-2-hydroxy-3-methoxy 3,3-diphenyl propionate

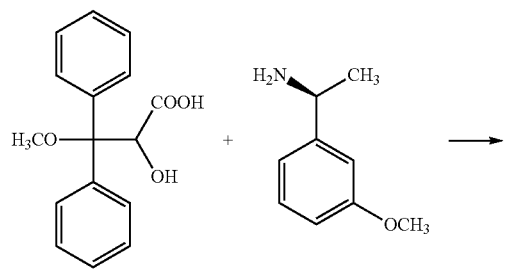

-continued

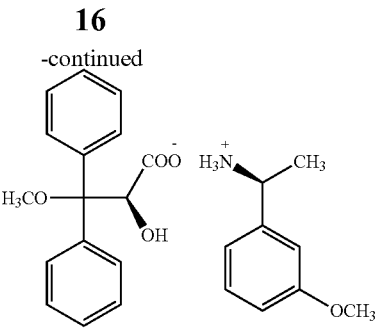

In 2 liter three necked flask, (90.0 g) (0.33 mole) 3,3-diphenyl-2-hydroxy-3-methoxy propionic acid and 0.9 liter acetonitrile was taken. Subsequently, the reaction mixture was stirred and heated at reflux temperature. (30 g) (0.198 mole) (S)-3-methoxy PEA, in 90 mL acetonitrile was added drop wise in 10 minute time interval. Further, the reaction mixture was stirred under reflux for 0.5 hr. The reaction mixture was cooled at room temperature and was stirred for 1.5 hour. Solid material was filtered, washed with acetonitrile and dried.

Yield: 65.0 g, (92.9%), HPLC purity: 99.82%, Chiral purity: 96.57%.

EXAMPLE 11

Purification of (S)-3-methoxypehenylethylammonium (S)-2-hydroxy-3-methoxy 3,3-diphenyl propionate In 0.3 liter three necked flask, (60 g) chiralamine salt and mixture of (1.350 L) ethanol and (150 mL) water was taken. Subsequently, the reaction mixture was stirred and heated at reflux temperature for 30 min. Solid material was precipitated at 60-65° C. and was cooled to room temperature. The reaction mixture was further stirred at 0-5° C. for 35-40 min. Solid material was filtered, washed with cold aqueous ethanol and dried.

Yield: 53.6 g, (89.3%). HPLC purity: 99.91%. Chiral purity: 100%.

IR (KBr): (3435 cm$^{-1}$, 2933 cm$^{-1}$, 2831 cm$^{-1}$, 2526 cm$^{-1}$, 2173 cm$^{-1}$, 1905 cm$^{-1}$, 1575 cm$^{-1}$, 1531 cm$^{-1}$, 1450 cm$^{-1}$, 1352 cm$^{-1}$, 1234 cm$^{-1}$, 1143 cm$^{-1}$, 1099 cm$^{-1}$, 1041 cm$^{-1}$, 964 cm$^{-1}$, 833 cm$^{-1}$, 773 cm$^{-1}$, 698 cm$^{-1}$, 632 cm$^{-1}$, 555 cm$^{-1}$.

$^1$H NMR (400 MHz, DMSO D$_6$): δ=8.00-6.87 (m, 17H), 4.72 (s, 1H), 4.18 (s, 1H), 3.74 (s, 3H), 3.17 (s, 3H), 1.39 (s, 3H).

$^{13}$C NMR (400 MHz, DMSO D$_6$) δ=21.422, 49.836, 51.625, 55.082, 73.083, 84.395, 112.251, 113.386, 118.688, 126.010, 126.560, 126.905, 128.332, 128.754, 129.612, 142.450, 143.666, 144.625, 159.367, 173.598.

MS: m/z=148.7 and 270.8 [M]

Figure 3:
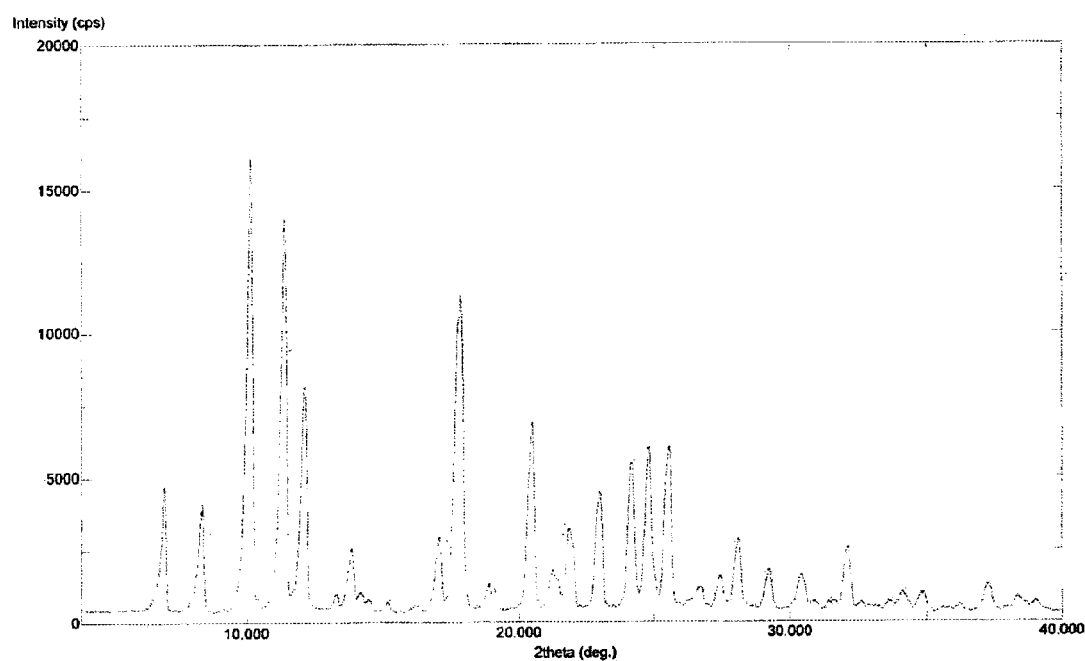
FIG. 3 is a powder X-ray diffraction (XRPD) pattern of the crystalline (S)-3-methoxyphenylethylammonium (S)-2-hydroxy-3-methoxy 3,3-diphenyl propionate according to the present invention.

PXRD peaks at about 7.05, 8.39, 10.15, 11.39, 12.15, 13.32, 13.87, 14.21, 14.51, 15.21, 17.07, 17.86, 18.87, 20.47, 21.25, 21.90, 23.01, 24.18, 24.80, 25.53, 26.69, 27.43, 28.09, 29.22, 30.43, 30.90, 31.43, 31.62, 32.12, 32.63, 33.64, 34.12, 34.84, 37.24, 38.34 and 39.04°±0.2° (2θ) (FIG. 3).

EXAMPLE 12

Preparation of (S)-3-methoxyphenylethylammonium (S)-2-hydroxy-3-methoxy 3,3-diphenyl propionate In 100 mL three necked flask, (5 g) (0.018 mole) 3,3-diphenyl-2-hydroxy-3-methoxy propionic acid and 50 mL rectified spirit was taken. Subsequently, the reaction mixture was stirred and heated at reflux temperature. (1.8 g) (0.011 mole) (S)-3-methoxy PEA, in 5 mL rectified spirit was added drop wise in 10 min. time interval. The reaction mixture was stirred under reflux for 0.5 hr and cooled to room temperature and again stirred at room temperature for 1.5 hour. Solid material was filtered, washed with rectified spirit and dried.

Yield: 3.3 g, (85.0%), HPLC purity: 99.91%, Chiral purity: 99.38%.

EXAMPLE 13

Preparation of (R)-2,4-dichlorophenylethylammonium (S)-2-hydroxy-3-methoxy 3,3-diphenyl propionate

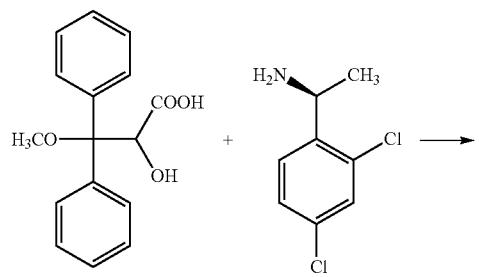

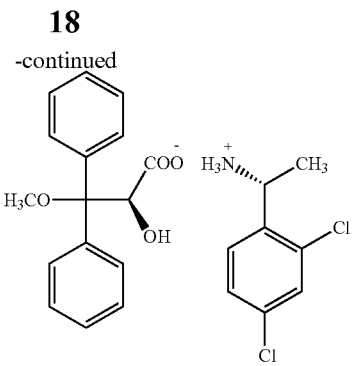

In a 5 liter three necked flask, (302 g) (1.10 mole) 3,3-diphenyl-2-hydroxy-3-methoxy propanoic acid and 3.02 liter acetonitrile was taken. Subsequently, the reaction mixture was stirred and heated at reflux temperature. (105.4 g) (0.55 mole) (R)-2,4-dichloro PEA, in 50 mL acetonitrile was added drop wise in 45 min. time interval Solid material was precipitated during this addition. The reaction mixture was stirred under reflux for 1 hr and cooled to room temperature. The reaction mixture was further stirred at room temperature for 1 hour. Solid material was filtered, washed with acetonitrile and dried.

Yield: 219 g, (85.41%), HPLC purity: 99.94%, Chiral purity: 95.01%.

Similarly, different diastereomeric salt of (S)-2-hydroxy-3-methoxy 3,3-diphenyl propionate was prepared using different chiral amine in different batches and the results are summarized in Table 2 given below.

TABLE 2

| EX. No. | Chiral amine | Input* g | Output g | % Purity HPLC | Chiral | % Yield | Solvent |
|---|---|---|---|---|---|---|---|
| 14 | (R)-2,4-dichloro PEA | 0.5 | 0.076 | 99.97 | 99.15 | 17.95 | MTBE + MeOH |
| 15 | (R)-2,4-dichloro PEA | 6.908 | 2.5 | 99.33 | 99.24 | 42.67 | MTBE + MeOH |
| 16 | (S)-3-methoxy PEA | 5 | 3.2 | 99.35 | 97.81 | 82.32 | Acetonitrile |
| 17 | (S)-4-chloro PEA | 2 | 1.115 | 99.18 | 95.40 | 71.02 | MTBE + MeOH |
| 18 | (R)-2,4-dichloro PEA | 1 | 0.510 | 99.95 | 99.74 | 60.0 | Acetonitrile |
| 19 | (R)-2,4-dichloro PEA | 60 | 43 | 99.95 | 99.20 | 84.41 | Acetonitrile |
| 20 | (R)-2,4-dichloro PEA | 127 | 168.5 | 99.61 | 97.91 | 93.09 | Acetonitrile |
| 21 | (S)-3-methoxy PEA | 10 | 7.2 | <98% | 96.51 | 92.6 | Acetonitrile |
| 22 | (S)-3-methoxy PEA | 70 | 52.2 | 99.93 | 96.82 | 95.9 | Acetonitrile |
| 23 | (S)-3-methoxy PEA | 5 | 3.3 | 99.9 | 99.38 | 85.0 | Rectified spirit |

*Input refers to 3,3-diphenyl-2-hydroxy-3-methoxy propionic acid

EXAMPLE 24

Purification of (R)-2,4-dichlorophenylethylammonium (S)-2-hydroxy-3-methoxy 3,3-diphenyl propionate In a 3 liter three necked flask, (100 g) chiral amine salt in mixture of 1.760 liter acetonitrile and 440 mL water was taken. The reaction mixture was stirred and heated under reflux to obtain a clear solution. This clear solution was transferred in 5 liter beaker and stored at −20° C. for 15 hours. Solid was filtered, washed with acetonitrile and dried.

Yield: 91 g (91%), HPLC purity: 99.84%. Chiral purity: 99.98%.

IR (KBr): (3466 $cm^{-1}$, 3055 $cm^{-1}$, 2974 $cm^{-1}$, 2935 $cm^{-1}$, 2875 $cm^{-1}$, 2831 $cm^{-1}$, 2540 $cm^{-1}$, 1637 $cm^{-1}$, 1591 $cm^{-1}$, 1539 $cm^{-1}$, 1479 $cm^{-1}$, 1442 $cm^{-1}$, 1404 $cm^{-1}$, 1352 $cm^{-1}$, 1097 $cm^{-1}$, 1045 $cm^{-1}$, 725 $cm^{-1}$, 696 $cm^{-1}$, 634 $cm^{-1}$, 1115 $cm^{-1}$, 677 $cm^{-1}$, 634 $cm^{-1}$, 546 $cm^{-1}$.

$^1$H NMR (400 MHz, DMSO $D_6$): δ=7.67 (d 1H), 7.60 (d, 1H), 7.47 (dd, 1H), 7.34 (dd, 4H), 7.23-7.12 (m, 6H), 4.84 (s, 1H), 4.47 (quartet, 1H), 1.31 (d, 3H)

$^{13}$C NMR (400 MHz, DMSO $D_6$) δ=21.719, 46.557, 51.976, 62.253, 73.250, 84.247, 99.599, 126.272, 126.334, 126.791, 127.160, 127.835, 128.254, 128.662, 128.757, 128.809, 132.464, 132.631, 136.947, 139.990, 143.139, 144.132, 173.405.

MS: m/z=270.8 [M−1]

Figure 4:
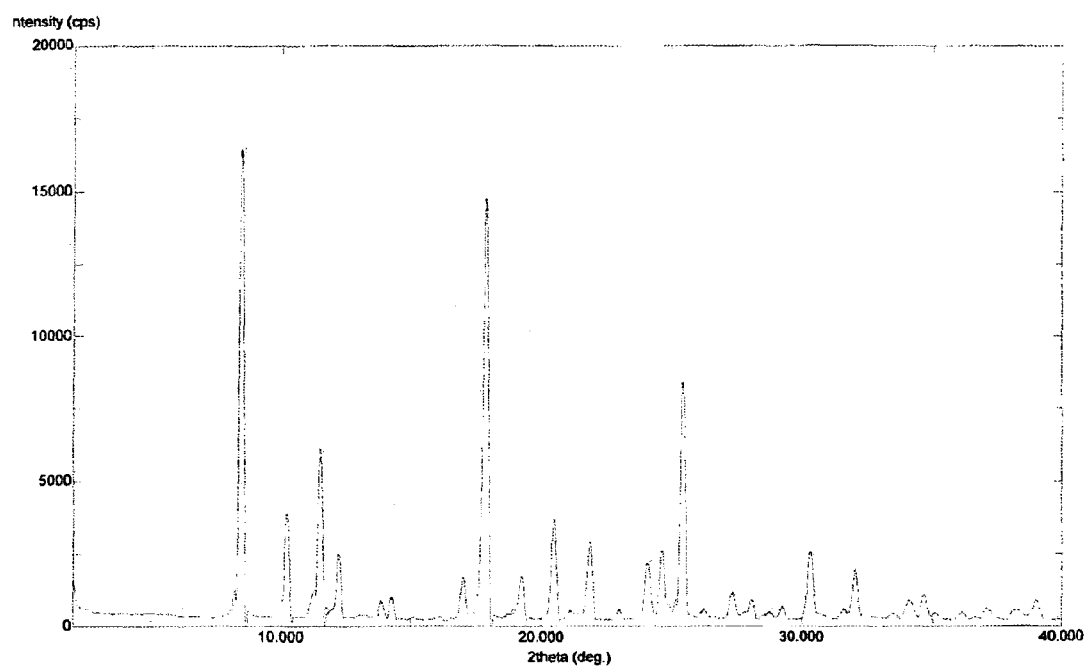
FIG. 4 is a powder X-ray diffraction (XRPD) pattern of the crystalline (R)-2,4-dichlorophenylethylammonium (S)-2-hydroxy-3-methoxy 3,3 diphenyl propionate according to the present invention.

PXRD peaks at about 8.49, 10.22, 11.51, 11.88, 12.22, 13.89, 14.30, 17.00, 17.86, 18.74, 19.25, 20.49, 21.13, 21.90, 23.03, 24.14, 24.69, 25.48, 26.27, 27.35, 28.09, 28.76, 29.26, 30.35, 31.65, 32.09, 33.51, 34.13, 34.68, 35.11, 36.13, 37.09, 38.14 and 39.02°±0.2° (2θ). (FIG. 4)

Similarly, purification of different diastereomeric salt of (S)-2-hydroxy-3-methoxy 3,3-diphenyl propionic acid using different solvent in different batches were done and the results are summarized in Table 3 given below.

EXAMPLE 38

Preparation Racemic Ambrisentan

In a 100 mL 3 necked flask, (2.24 g) (0.0057 mol) racemic Ambrisentan methyl ester was taken. Subsequently, 22.4 mL of 1, 4 dioxane was added & stirred the reaction mixture. Aqueous solution of (2.35 g) of sodium hydroxide dissolved in 15 mL water was added in to the reaction mixture and was gently refluxed for 3 hrs. The reaction mixture was cooled and dumped into water. After suitable work up racemic Ambrisentan was obtained.

Yield: 1.6 g (74.07%), HPLC purity: 99.06%.

Similarly, racemic Ambrisentan was prepared in different batches and the results are summarized in Table 4 given below.

TABLE 4

| Ex. No. | Input g | Output g | % HPLC Purity | % Yield | Solvent |
|---|---|---|---|---|---|
| 39 | 2.24 | 1.6 | 99.06 | 74.07 | Dioxane |

EXAMPLE 40

Preparation (R)-Ambrisentan

In a 25 mL three necked flask, (0.150 g) (S) 2,4-dichlorophenethyl ammonium salt of (S) 2-hydroxy-3-methoxy 3,3-diphenyl propionate, 22.68 mg lithium hydride and 3 mL DMF were taken. Subsequently, (76 mg) 4,6-dimethyl-2-methylsulfonyl pyrimidine was added in to the reaction mixture. Reaction mixture was stirred at 30-32° C. for 48 hours and diluted with water. After suitable work up and acidification gives 94.7 mg (R)-Ambrisentan.

TABLE 3

| Sr. No. | Chiral amine | Input* g | Output g | % Purity HPLC | % Purity Chiral | % Yield | Solvents |
|---|---|---|---|---|---|---|---|
| 25 | (S)-3-methoxy PEA | 0.5 | 0.417 | 99.43 | 99.91 | 83.4 | Isopropanol |
| 26 | (S)-3-methoxy PEA | 0.5 | 0.421 | 99.52 | 99.97 | 84.2 | Isopropanol and water |
| 27 | (S)-3-methoxy PEA | 0.5 | 0.425 | 99.43 | 99.17 | 85 | Isopropanol |
| 28 | (R)-2,4-dichloro PEA | 11.5 | 8.5 | 100 | 100 | 73.9 | Acetonitrile and water |
| 29 | (R)-2,4-dichloro PEA | 43 | 35 | 99.76 | 100 | 81.39 | Acetonitrile and water |
| 30 | (R)-2,4-dichloro PEA | 64 | 51 | 99.76 | 100 | 79.68 | Acetonitrile and water |
| 31 | (R)-2,4-dichloro PEA | 10 | 7.3 | 99.74 | 100 | 73.0 | Acetonitrile and water |
| 32 | (S)-3-methoxy PEA | 1 | 0.71 | 99.87 | 100 | 71.0 | Methanol and water |
| 33 | (S)-3-methoxy PEA | 1 | 0.89 | 99.91 | 100 | 89 | Ethanol and water |
| 34 | (S)-3-methoxy PEA | 1 | 0.81 | 99.87 | 100 | 81.4 | Ethanol and water |
| 35 | (S)-3-methoxy PEA | 7.0 | 6.0 | 99.52 | 100 | 86.0 | Ethanol and water |
| 36 | (S)-3-methoxy PEA | 52 | 46.7 | 99.88 | 100 | 89.8 | Ethanol and water |
| 37 | (S)-3-methoxy PEA | 95 | 74.1 | 99.95 | 100 | 78.0 | Ethanol and water |

*Input refers to diastereomeric salt of 3,3-diphenyl-2-hydroxy-3-methoxy propionic acid Similarly, (R)-Ambrisentan was prepared in different batch and the results are summarized in Table 5 given below.

TABLE 5

| Sr. No. | Input g | Output g | % Purity HPLC | Chiral | % Yield | Base/Solvent |
|---|---|---|---|---|---|---|
| 41 | 0.15 | 0.094 | 90.37 | 96 | 77.14 | LiNH$_2$/DMF |

EXAMPLE 42

Preparation of Ambrisentan

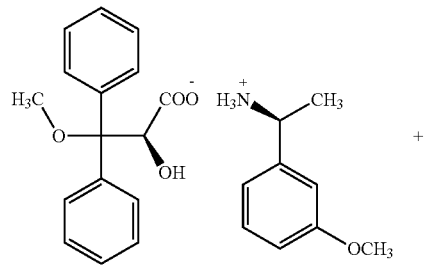

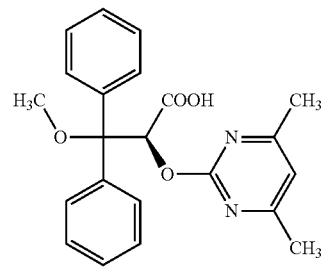

In a 1 liter four necked flask, (73.5 g) (0.17 mole) (S)-3-methoxyphenylethylammonium (S)-2-hydroxy-3-methoxy 3,3-diphenyl propionate, (50 g) sodium t-butoxide and 367.5 mL DMF were taken at room temperature. Reaction mixture was cooled to 20° C. then 48.5 g 4,6-dimethyl-2-methylsulfonyl pyrimidine was added. The reaction mixture was stirred at 30° C. for 3 hrs and subsequently dumped in water and again stirred for 10 min. The reaction mixture was extracted with cyclohexane, charcoalised and acidified to get crude Ambrisentan.

Yield: 59.7 g (90.9%), HPLC Purity: 98.79%, Chiral purity: 99.92%.

Similarly crude Ambrisentan was prepared in different batches using (R)-2,4-dichloro PEA salt or (S)-3-methoxy PEA salt and the results are summarized in Table 6 given below.

TABLE 6

| Ex. No. | Chiral amine | Input* g | Output g | % Purity HPLC | Chiral | % Yield | Solvent/base |
|---|---|---|---|---|---|---|---|
| 43 | (R)-2,4-Dichloro PEA | 35 | 25 | 98.86 | 99.90 | 87.27 | DMF and LiNH$_2$ |
| 44 | (R)-2,4-Dichloro PEA | 51 | 37 | 99.04 | 100 | 88.6 | DMF and LiNH$_2$ |
| 45 | (R)-2,4-Dichloro PEA | 1 | 0.42 | 96.90 | — | 51.32 | DMF and Na t butoxide |
| 46 | (R)-2,4-Dichloro PEA | 1 | 0.35 | 95.83 | — | 42.76 | Na t butoxide and DMSO |
| 47 | (R)-2,4-Dichloro PEA | 1 | 0.36 | 98.52 | — | 43.98 | Na-t-butoxide and dimethyl acetamide |
| 48 | (S)-3-methoxy PEA | 1 | 0.74 | 98.35 | 100 | 83.31 | Na-t-butoxide and DMF |
| 49 | (S)-3-Methoxy PEA | 5 | 3.5 | 97.96 | 99.95 | 78.3 | Na-t-butoxide and DMF |
| 50 | (S)-3-Methoxy PEA | 18 | 14.6 | 99.18 | 99.87 | 90.7 | Na-t-butoxide and DMF |
| 51 | (S)-3-Methoxy PEA | 73.5 | 59.7 | 98.79 | 99.92 | 90.90 | Na-t-butoxide and DMF |
| 52 | (S)-3-Methoxy PEA | 20 | 15.8 | 99.23 | 100 | 88.37 | Na-t-butoxide and DMF. Temperature −10° C. |

*Input refers to diastereomeric salt of 3,3-diphenyl-2-hydroxy-3-methoxy propionic acid -continued

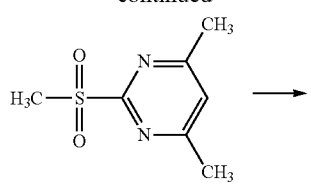

EXAMPLE 53

Process for the Purification of Ambrisentan

In 500 mL three necked flask, (29.5 g) (0.077 moles) crude Ambrisentan and 206.5 mL DM water was taken at room temperature. Subsequently, 45 mL 10% sodium hydroxide solution was added to obtained clear solution. (1.475 g) activated charcoal was added and stirred the reaction mixture at room temperature. The reaction mixture was filtered through hyflow and washed with water. Clear filtrate was acidified with dilute hydrochloric acid to precipitate the solid mass, which was filtered and dried.

Yield: 27.5 g (93%), HPLC purity: 99.52%, Chiral purity: 99.91%.

Similarly crude Ambrisentan was purified in different batches and the results are summarized in Table 7 given below.

TABLE 7

| Ex. No. | Input g | Output g | % Purity HPLC | % Purity Chiral | % Yield |
|---|---|---|---|---|---|
| 54 | 5 | 4.5 | 99.71 | 99.83 | 90 |
| 55 | 20 | 18.5 | 99.51 | 99.90 | 92.5 |
| 56 | 18.5 | 17.8 | 99.80 | 99.90 | 96.21 |
| 57 | 29.5 | 27.5 | 99.52 | 99.91 | 93.22 |

EXAMPLE 58

Process for the Purification of Ambrisentan

In a 500 mL three necked flask, (26.2 g) (0.069 mole) Ambrisentan (obtained after first purification) and 183.4 mL ethanol was taken. The reaction mixture was heated with stirring to obtain a clear solution. Subsequently, 131 mL DM water was added and stirred under reflux for 30-45 minute. The reaction mixture was allowed to cool to precipitate solid mass after some time. The reaction mixture was again stirred at 25-30° C. for 45 min. Solid was filtered and dried.

Yield: 22.0 g (84%), HPLC purity: 99.63%, Chiral purity: 99.87%.

IR (KBr): (3057 cm$^{-1}$, 2966 cm$^{-1}$, 2835 cm$^{-1}$, 1753 cm$^{-1}$, 1597 cm$^{-1}$, 1558 cm$^{-1}$, 1444 cm$^{-1}$, 1406 cm$^{-1}$, 1379 cm$^{-1}$, 1301 cm$^{-1}$, 1192 cm$^{-1}$, 1114 cm$^{-1}$, 1053 cm$^{-1}$, 972 cm$^{-1}$, 748 cm$^{-1}$, 700 cm$^{-1}$, 609 cm$^{-1}$, 549 cm$^{-1}$.

$^1$H NMR (400 MHz, DMSO D$_6$): δ=12.54 (s 1H), 7.35-7.18 (m, 10H), 6.92 (s 1H), 6.16 (s, 1H), 3.38 (s, 3H), 2.33 (s, 6H).

$^{13}$C NMR (400 MHz, DMSO D$_6$) δ=23.328, 53.025, 77.587, 83.168, 114.751, 126.978, 126.991, 127.234, 127.667, 127.714, 127.846, 141.461, 142.635, 163.201, 169.050, 169.061.

MS: m/z=378.9 [M$^+$]

PXRD peaks at about 7.48, 8.86, 12.25, 12.96, 13.99, 15.04, 15.45, 16.61, 17.73, 18.14, 18.14, 18.66, 19.37, 20.46, 21.89, 22.93, 23.20, 24.17, 25.12, 25.43, 26.29, 26.73, 27.41, 28.22, 28.76, 29.25, 29.88, 30.33, 31.85, 32.10, 32.73, 33.92, 34.74, 35.90, 36.55, and 38.35°±0.2° (2θ).

Similarly crude Ambrisentan was purified in different batches and the results are summarized in Table 8 given below.

TABLE 8

| Sr. No. | Input g | Output g | % Purity HPLC | % Purity Chiral | % Yield |
|---|---|---|---|---|---|
| 59 | 14.5 | 11.7 | 99.62 | 99.91 | 80.65 |
| 60 | 3.4 | 2.7 | 99.50 | 99.97 | 79.41 |
| 61 | 11.6 | 9.8 | 99.68 | 99.89 | 84.5 |
| 62 | 2.6 | 2.1 | 99.77 | 100 | 80.76 |

While the present invention has been described in terms of its specific embodiments, certain modifications and equivalents will be apparent to those skilled in the art and are intended to be included within the scope of the present invention.

The invention claimed is:

1. A process for preparing Ambrisentan of formula (I),

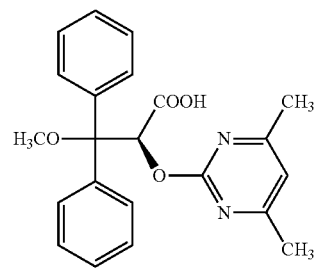

(I)

the process comprising:
a) resolving racemic 2-hydroxy propanoic acid of formula (VIII),

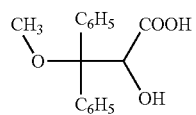

Formula VIII with chiral amine of formula (IX),

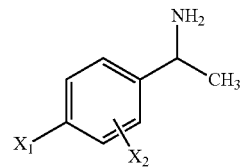

Formula IX with either in (S) or (R) configuration, wherein X$_1$ is selected from hydrogen, halogen, (C$_1$-C$_4$) alkyl or (C$_1$-C$_4$) alkoxy group and X$_2$ is selected from halogen, (C$_1$-C$_4$) alkyl or (C$_1$-C$_4$) alkoxy group; to obtain a diastereomeric salt of 2-hydoxypropanoic acid of Formula (II)

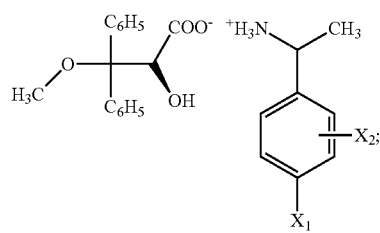

II and
b) reacting the diastereomeric salt of 2-hydoxypropanoic acid of Formula (II) in either (S) or (R) configuration, wherein X$_1$ is selected from hydrogen, halogen, (C$_1$-C$_4$) alkyl or (C$_1$-C$_4$) alkoxy group and X$_2$ is selected from halogen, $(C_1-C_4)$ alkyl or $(C_1-C_4)$ alkoxy group, with 4,6-dimethyl-2-(methylsulfonyl) pyrimidine of Formula (VII), Formula (VII)

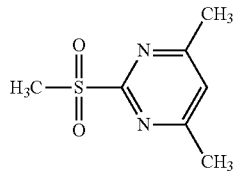

to obtain the ambrisentan of Formula (I).

2. The process of claim 1, wherein the resolution of racemic 2-hydroxypropanoic acid of Formula (VIII) is carried out in the presence of at least one suitable solvent.

3. The process of claim 2, wherein the suitable solvent comprises at least one member selected from the group consisting of water, DMSO, DMF, acetonitrile, diethyl ether, 1,4-dioxane, MTBE, 2-methyl THF, dimethyl acetamide, DCM, DIPE, THF, and $(C_1-C_6)$ alcohols.

4. The process of claim 1, wherein the reaction of the diastereomeric salt of 2-hydoxypropanoic acid of Formula (II) with 4,6-dimethyl-2-(methylsulfonyl) pyrimidine of Formula (VII) is carried out in the presence of at least one suitable base.

5. The process of claim 4, wherein the suitable base comprises at least one member selected from the group consisting of lithium diisopropyl amide, sodium amide, sodium carbonate, sodium bicarbonate, potassium carbonate, sodium hydroxide, potassium hydroxide, tripotassium phosphate, LHMDS, KHMDS, potassium tert-butoxide, and sodium tert-butoxide.

6. The process of claim 1, wherein step (b) is carried out at a temperature of from about −10° C. to room temperature.

7. The process of claim 1, wherein the compound of Formula (II) is recrystallized prior to condensation with 4,6-dimethyl-2-(methylsulfonyl) pyrimidine of Formula (VII).

* * * * *